(12) United States Patent
Bogue

(10) Patent No.: US 7,493,694 B2
(45) Date of Patent: Feb. 24, 2009

(54) METHOD OF MANUFACTURING A PROSTHETIC SUCTION SOCKET

(75) Inventor: David Bogue, Layton, NJ (US)

(73) Assignee: Pro-Med, Inc., Layton, NJ (US)

( * ) Notice: Subject to any disclaimer, the term of this patent is extended or adjusted under 35 U.S.C. 154(b) by 664 days.

(21) Appl. No.: 11/183,013

(22) Filed: Jul. 15, 2005

(65) Prior Publication Data

US 2006/0010690 A1 Jan. 19, 2006

Related U.S. Application Data

(60) Provisional application No. 60/589,226, filed on Jul. 19, 2004.

(51) Int. Cl.
*B29C 37/00* (2006.01)
*A61F 2/38* (2006.01)
(52) U.S. Cl. .............................. 29/898.049; 623/20.22
(58) Field of Classification Search .......... 29/898.049, 29/898.048; 264/239, 161, 139, 259, 162; 623/20.22
See application file for complete search history.

(56) References Cited

U.S. PATENT DOCUMENTS

| 5,756,027 A | 5/1998 | Rothschild et al. ........... 264/138 |
| 6,287,345 B1 | 9/2001 | Slemker et al. ............... 623/34 |
| 6,797,008 B1 | 9/2004 | Arbogast et al. ............... 623/34 |
| 6,979,355 B1 | 12/2005 | Slemker ........................ 623/34 |
| 2002/0055383 A1* | 5/2002 | Onda et al. .................... 463/36 |

* cited by examiner

*Primary Examiner*—John C Hong
(74) *Attorney, Agent, or Firm*—Harness, Dickey & Pierce, P.L.C.

(57) ABSTRACT

A method of manufacturing a prosthetic socket having an access port that employs a housing with a cylindrical extension. The method includes the step of molding a shell over a socket model and a mold dummy to form an intermediate port. The method additionally includes the step of trimming the intermediate port along a trim line passing through a cavity defined by the mold dummy to create a circular opening in the shell. The mold dummy has a first diameter generally conforming to a diameter of the cylindrical extension of the housing. The method further includes the steps of passing the cylindrical extension through the opening and securing the access port to the shell.

16 Claims, 2 Drawing Sheets

METHOD OF MANUFACTURING A PROSTHETIC SUCTION SOCKET

CROSS-REFERENCE TO RELATED APPLICATIONS

This application claims the benefit of U.S. Provisional Application No. 60/589,226, filed on Jul. 19, 2004. The disclosure of the above application is incorporated herein by reference.

FIELD OF THE INVENTION

The present invention generally relates to prosthetic suction socket suspension systems. More particularly, the present invention relates to a socket port for a prosthetic suction socket suspension system. The present invention also pertains to a related method of manufacture.

BACKGROUND OF THE INVENTION

Various prosthetic devices for limb replacement are known in the art. Many such prosthetic devices include a socket that serves as the connection between the user (amputee) and the prosthesis. For load bearing prostheses (e.g., lower limb prostheses, such as above knee prostheses), the weight of the amputee is transferred to the ground through the socket.

For most patients, a socket-type prosthesis can be held in place by a negative pressure or vacuum created between the close fit of a residual limb and the socket. The successful fitting of a prosthetic socket results in the effective transfer of forces from the socket to the residual limb such that the amputee can maintain daily activities without tissue damage or pain.

While significant advancements have been made in the field of prosthetic sockets in recent years, all known devices are associated with certain limitations. In this regard, prosthetic sockets are not designed to maintain suitable vacuum for high vacuum socket systems. In this regard, known high vacuum socket systems generally achieve a vacuum in the range of approximately 15-25 inches of mercury. Access plugs for such socket systems do not sufficiently seal with the shell to maintain this high level vacuum. Additionally, known prosthetic sockets cannot alternatively be used for high vacuum applications by incorporating a plug and standard vacuum applications by incorporating a valve.

A need remains in the art for a prosthetic socket which overcomes the limitations associated with the prior art, including but not limited to those limitations discussed above.

SUMMARY OF THE INVENTION

In one form, the present invention provides a method of manufacturing a prosthetic socket having an access port. The access port has a housing with a cylindrical extension. The method includes the step of molding a shell over a socket model and a mold dummy to form an intermediate port. The method additionally includes the step of trimming the intermediate port along a trim line passing through a cavity defined by the mold dummy to create a circular opening in the shell. The mold dummy has a first diameter generally conforming to a diameter of the cylindrical extension of the housing. The method further includes the steps of passing the cylindrical extension through the opening and securing the access port to the shell.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE EMBODIMENTS

The following description of the embodiments of the present invention is merely exemplary in nature and is in no way intended to limit the invention, its application, or uses.

Figure 1:
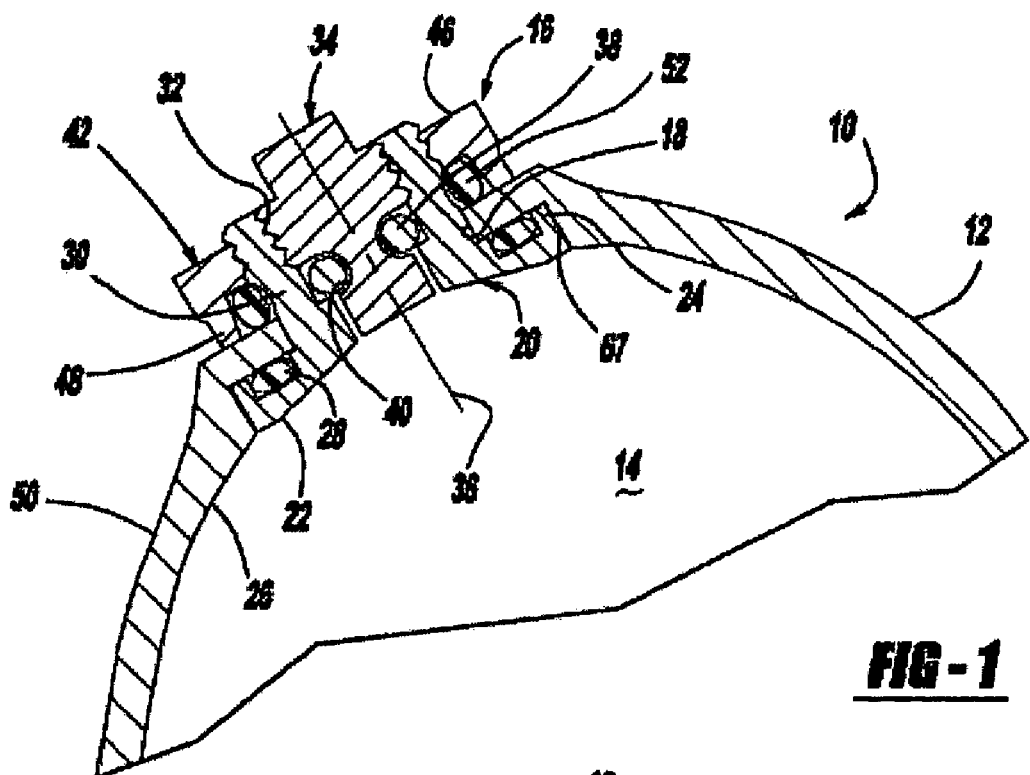
FIG. 1 is a cross-sectional view of a portion of a prosthetic socket taken through an access port of the prosthetic socket.

With initial reference FIG. 1, a prosthetic socket constructed in accordance with the teachings of the present invention is illustrated and generally identified at reference character 10. As described below, the prosthetic socket may be used for a high vacuum application. It will be noted, however, that the teachings of the present invention are not so limited.

The prosthetic socket 10 of the present invention may generally include a socket shell 12. The socket shell 12 defines an interior 14 for receiving the residual limb (not shown) of the amputee. In one particular application, the socket shell 12 may be vacuum formed of a thermoplastic material. Those skilled in the art, however, will readily appreciate that other materials having suitable strength, flexibility, and durability characteristics may be alternatively used.

The prosthetic socket 10 may further generally include an access port 16. The access port 16 facilitates pull-in access for donning the prosthesis. The access port 16 may be secured to the shell 12 at an opening 18 and may include a base or housing 20. The housing 20 may include a lower flange portion 22 having a circular lip 24 that projects toward an inner surface 26 of the shell 12. A gap may be defined by the lower flange portion 22 and the circular lip 24 which accommodates an O-ring seal 28. The O-ring seal 28 can be compressed against the inner surface 26 of the shell 12.

The housing 20 may further include a cylindrical extension 30 that extends through the opening 18 of the shell 12. The cylindrical extension 30 may define a cylindrical opening 32 that receives an access plug 34. The access plug 34 may be inserted into the cylindrical opening 32 along a centerline axis 36. As shown, the access plug 34 seals the interior 14 of the shell 12. The access plug 34 may be removed for donning or to allow air into the interior 14 of the shell 12 through the opening 18. An O-ring seal 38 may be carried within a circumferentially defined groove 40 of the access plug 34.

The housing 20 of the access port 16 may be secured to the shell 12 by a clamp nut 42. In this regard, the clamp nut 42 may define an opening 18 that threadably engages the cylindrical extension 30 of the housing 20. The clamp nut 42 may include an upper flange portion 46 having a circular lip 48 that projects toward an outer surface 50 of the shell 12. A gap may be defined by the upper flange portion 46 and the circular lip 48 which accommodates an O-ring seal 52. The O-ring seal 52 may be compressed against the outer surface 50 of the shell 12.

Figure 2:
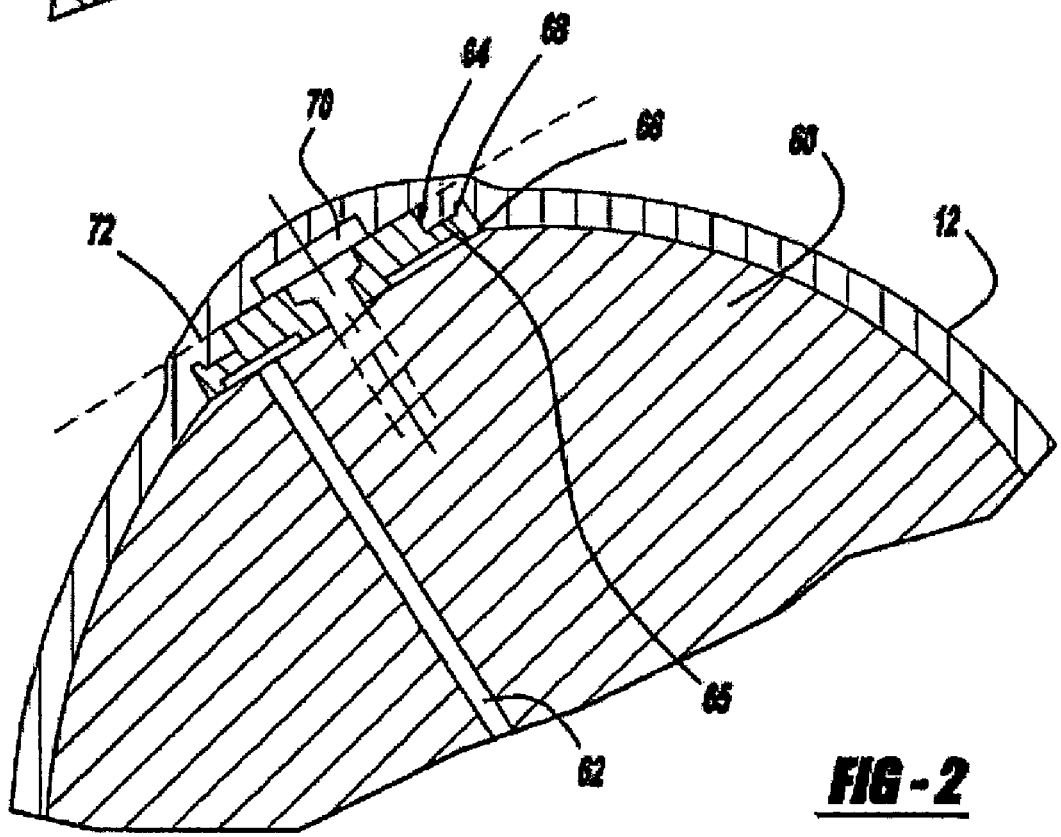
FIG. 2 is a cross-sectional view similar to FIG. 1, illustrating the shell of the prosthetic socket after molding and prior to trimming and introduction of the access port.

Turning to the cross-sectional view of FIG. 2, a portion of the shell 12 of the prosthetic socket 10 is shown after vacuum molding but prior to trimming and installation of the access port 16. The shell 12 may be vacuum formed about a socket model 60. The socket model 60 may define a vacuum vent hole 62 and may be generally shaped to conform to the desired configuration of the interior 14 of the shell 12.

The shell 12 may be specifically configured to accommodate the access port 16 through use of a mold dummy 64. The mold dummy 64 may create the exact shape and hole diameter to match the housing 20 (with O-ring 28 fitted on the access port 16) of the access port 16. In this manner, the housing 20 may facilitate optimum compression on the O-ring seal 28 and thereby provides reliable sealing of the access port 16 to a minimum of 27 inches of mercury. The outer O-ring seal 52 primarily provides sealing redundancy.

The mold dummy 64 may define a vent hole 65 and may include an upper diameter and a lower diameter. The upper diameter may generally conform in size to the cylindrical extension 30 of the housing 20. The lower diameter may generally conform in size to the countersunk recess 67 defined on the inner surface 26 of the shell 12. The mold dummy 64 may have a downwardly extending cylindrical lip 66 and an upwardly extending cylindrical lip 68. The downwardly extending lip 66 may define the depth of the countersunk recess 67. The upwardly extending cylindrical lip 68 may define a groove that receives the lip 24 of the housing 20 thus providing a radial lock between the housing 20 and the shell 12. A foam cover disc 70 may be placed upon the mold dummy 64 during molding. The mold dummy 64 may be screwed, pinned or otherwise suitably attached to the socket model 60.

After the shell 12 is vacuum molded to the shape shown in FIG. 2 and allowed to suitably cool, the shell may be trimmed along a trim line 72. The trim line 72 may pass through a cavity formed by the mold dummy 64. Trimming along the trim line opens the opening 18 (see FIG. 1) for introduction of the access port 16.

Figure 3:
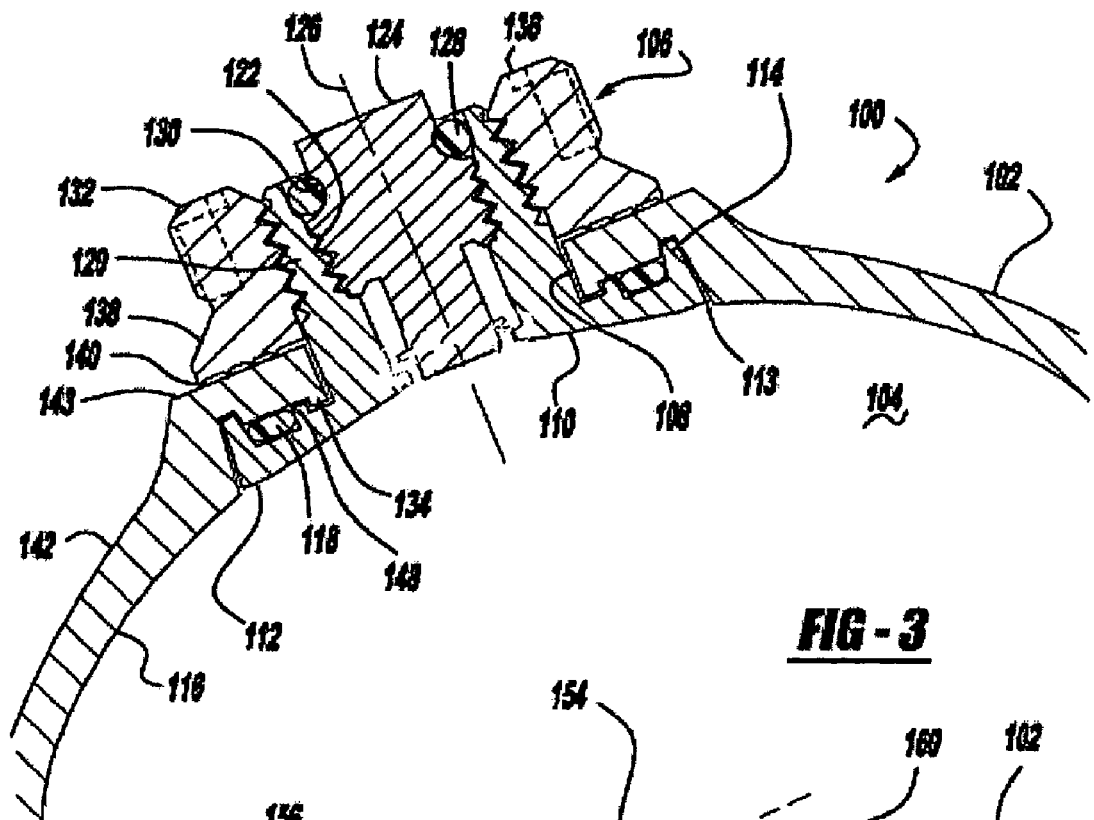
FIG. 3 is a cross-sectional view of a portion of a prosthetic socket of a second embodiment taken through an access port of the prosthetic socket.

FIG. 3 depicts a second embodiment of a prosthetic socket 100. The prosthetic socket 100 of FIG. 3 is similar to the prosthetic socket of FIG. 1; however, distinct advantages of the prosthetic socket 100 of the present embodiment will be made evident. A description of the operative workings of the prosthetic socket according to the second embodiment will now be described.

The prosthetic socket 100 of FIG. 3 may provide the same prosthetic socket access port as the socket of FIG. 1. The socket 100 can be used with valves as well as plugs. Additionally, the socket 100 installs reliably in super flexible socket materials and rigid socket port materials. This added functionality of accommodating either flexible or rigid materials means that the socket 100 can be reliably installed in materials such as polypropylene (PP), which is a very rigid plastic, low density polyethylene (PE), which is a soft and flexible thermoplastic, and silicon, which is soft and flexible and used as a padding material in sockets. While the socket 100 is primarily designed for conventional suction sockets, the system will work in high vacuum sockets, which increases its attractiveness with regard to multiple applications.

The prosthetic socket 100 of the teachings of the second embodiment may include a socket shell 102. The socket shell 102 defines an interior 104 for receiving a residual limb (not shown) of the amputee. The socket shell 102 may be vacuum formed from a thermoplastic material, although those skilled in the art will appreciate that other suitable materials may be used.

The prosthetic socket 100 may include an access port 106. The access port 106 may facilitate pull-in access for donning the prosthesis. The access port 106 may be secured to the shell 102 at an opening 108 and may include a base or housing 110. The housing 110 may include a lower flange portion 112 that is responsible for locking and sealing with the shell 102. More specifically, the lower flange portion 112 may contain, on its top side, an outer lip 114, also known as a lock rib 114, an intermediate lip 148, a recession for an O-ring seal 118, and a recession for a shell lip 134, also known as a shell lock rib 134. The shell 102 may contain a countersink recession 113 to better accommodate the fitting and assembly of the outer lip 114, the tip of which protrudes toward the inner surface of the shell 102 to fit into a further recession of the shell 102.

To facilitate sealing of the housing 110 with the shell 102, the O-ring seal 118 may be interposed and compresses between the outer lip 114 and the intermediate lip 148. The intermediate lip 148 may abut against the shell lip 134, which abuts against the cylindrical extension of the housing 110. In concert, the outer lip 114, intermediate lip 148 and shell lip 134, may all work together to prevent movement.

The housing 110 may further include a cylindrical extension 120 that extends through the opening 108 of the shell 102. The cylindrical extension 120 may define a cylindrical opening 122 that receives a closure member 124. The closure member may be in the form of an access plug 124, as shown in the drawings. The closure member 124 may also be in the form of a valve. The closure member 124 may be inserted into the cylindrical opening 122 along its axis 126. As depicted in FIG. 3, the closure member 124 may seal the interior 104 of the shell 102 in a variety of ways. The closure member 124 may be equipped with an O-ring seal 128 that is accommodated within a groove 130 of the O-ring. The O-ring seal 128 may be compressed within the groove 130 and abut against an end bore of the cylindrical extension 120 to create a seal when the closure member 124 is tightened. The access plug 124 may be removed for donning or to allow air into the interior 104 of the shell 102 through the opening 108.

The housing 110 of the access port 106 may be secured to the shell 102 by a clamp nut 132. In this regard, the clamp nut 132 may define an opening 108 that threadably engages the cylindrical extension 120 of the housing 110. The clamp nut 132 may include an upper flange portion 136 having a clamping flange 138 that projects toward an outer surface 142 of the shell 102. The clamping flange 138 may have a plurality of circular ridges 140 on its face that face a clamping land 143 of the outer surface 142 of the shell 102. The circular ridges 140 may provide an even distribution of the clamping force of the clamp nut 132 against the clamping land 143. The force of the clamping nut 132 may bear against the shell 102 and the lower flange portion 112 which ultimately causes the compression of the O-ring seal 118 between the shell 102, the lower flange portion 112, the intermediate lip 148, and the outer lip 114. Additionally, the shell lip 134 and the intermediate lip 148 may overlap and abut to provide radial locking of the device. Such is also the effect of the outer lip 114 within the shell 102. In this manner, the housing 110 may be prevented from moving laterally within the socket 100.

In addition to the forgoing advantages related to movement and sealing, parts may be also eliminated. More specifically, the O-ring seal 52 and the associated machining necessary to accommodate it within the clamp nut 42 are eliminated. This may provide a cost and part count reduction.

Figure 4:
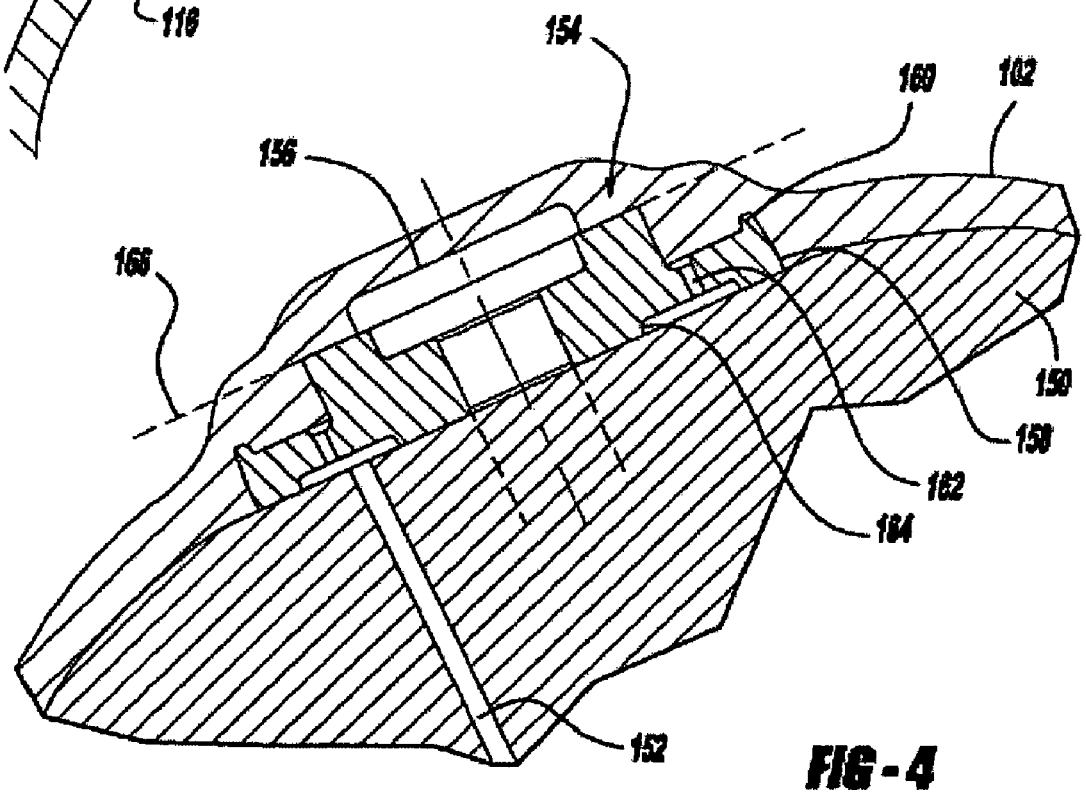
FIG. 4 is a cross-sectional view similar to FIG. 3, illustrating the shell of the prosthetic socket after molding and prior to trimming and introduction of the access port for the second embodiment.

Turning to the cross-sectional view of FIG. 4, a portion of the shell 102 of the prosthetic socket 100 is shown after vacuum molding but prior to trimming and installation of the access port 106. Similar to the first embodiment, the shell 102 may be vacuum formed about a socket model 150. The socket model 150 may define a vacuum vent hole 152, which vents the vent area 164, the socket model being generally shaped to conform to the desired configuration of the interior 104 of the shell 102.

The shell 102 may be specifically configured to accommodate the access port 106 through use of a mold dummy 154. The mold dummy 154 may create the exact shape and hole diameter to match the housing 110 of the access port 106. The mold dummy 154 may also account for space to fit the O-ring seal 118 of the housing 110. In this manner, the housing 110 may facilitate optimum compression on the O-ring seal 118 and thereby provides reliable sealing of the access port 106 to a minimum of 27 inches of mercury. The prosthetic socket 100 of the second embodiment as depicted in FIG. 3, departs from the prosthetic socket 10 of the first embodiment depicted in FIG. 1, wherein the outer O-ring seal 52 of the first embodiment, which primarily provides sealing redundancy, is not necessary on the second embodiment.

Furthermore, the mold dummy 154 may define a vent hole 162 and may have an upper diameter and a lower diameter. The upper diameter may generally conform in size to the cylindrical extension 120 of the housing 110. The lower diameter may generally conform in size to the countersunk recess 113 defined on the inner surface 116 of the shell 102. The mold dummy 154 may have a downwardly extending cylindrical lip 158 and an upwardly extending cylindrical lip 160. The downwardly extending lip 158 may define the depth of the countersunk recess 113. The upwardly extending cylindrical lip 160 may define a groove that receives the outer lip or lock rib 114 of the housing 110 thus providing a radial lock between the housing 110 and the shell 102. A foam cover disc 156 may be placed upon the mold dummy 154 during molding. The mold dummy 154 may be screwed, pinned or otherwise suitably attached to the socket model 150.

After the shell 102 is vacuum molded to the shape shown in FIG. 4 and allowed to suitably cool, the shell 102 may be trimmed along a trim line 166. The trim line 166 passes through a cavity formed by the mold dummy 154. Trimming along the trim line 166 opens the opening 108 (see FIG. 3) for introduction of the access port 106.

In one particular application, the prosthetic sockets 10, 100 described above are for a high vacuum, lower limb, above knee prosthesis. It will be understood, however, that the teachings of the present invention are also applicable for other applications. For example, in one alternative application, the sockets 10, 100 may be used for conventional suction socket applications by replacing the plug 34, 124 with a valve (not particularly shown). Other applications will be apparent to those of ordinary skill in the art.

While the component parts of a prosthetic socket 10,100 according to the teachings of the present invention are described above, a method of manufacturing the prosthetic socket is also known. According to the teachings of the present invention, manufacturing a prosthetic socket 10, 100 having an access port 16,106 entails determining a valve location on a socket model 60, 150 and flattening or leveling an area to ensure that the mold dummy 64, 154 sits flush or flat. A pilot hole may be drilled into the socket model for mounting the mold dummy 64, 154 to the socket model 60, 150 with a screw (not shown). Additionally, a vacuum hole 62, 152 may be drilled adjacent to the pilot hole and extends to the bottom of the cast model. Next, the mold dummy may be mounted with small air holes in a position over the pilot and vacuum holes. The self-adhesive foam disk 70, 156 may be placed over the screw head.

After mounting the self-adhesive foam disk, the heated thermoplastic material 12, 102 may be guided around the mold dummy in a fashion to blister or drape mold the thermoplastic socket 12,102. The heated plastic may be permitted to cool and a disc sander or equivalent material removing device may be used to remove enough plastic to permit removal of the self-adhesive disc 70, 156 and screw. Sanding or an equivalent material removing method may be continued until the face of the mold dummy 64, 154 is slightly scuffed and the cast plastic is flush with the dummy face, as noted by the trim line 72, 166. This method results in a smooth and flush interface surface of the mold dummy 64, 154 and its corresponding socket shell 12,102, that is, the cast plastic.

The socket model 60, 150 and the mold dummy 64, 154 may be removed from the cast model 12, 102 upon cooling of the cast, and the housing 20, 110 may be inserted through the socket shell 12, 102 from the mold dummy side, the housing having an O-ring seal 28, 118 installed in it before its insertion to ensure proper sealing. The clamp nut 42, 132 may be screwed onto the cylindrical extension 30, 120 of the housing 20, 110 and the nut is tightened. To complete the installation, the access plug 34, 124 or valve may be inserted and turned to tighten it within the cylindrical opening 32, 122 of the cylindrical extension 30, 120.

Advantages of the D-Loc System are its suitability for super flexible and rigid socket materials, its broad clamping flange 138, its second locking groove adjacent the cylindrical extension 120, and an aggressive outer locking rib 114 on the housing 110. The broad, ribbed face on the clamp nut 132 provides a broader clamping surface area than other socket access ports. Finally, the outer O-ring seal 52 of the socket of FIG. 1, which primarily provides redundant sealing, is not necessary with the second embodiment of FIG. 3.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A method of manufacturing a prosthetic socket having an access port, the method of manufacturing comprising the steps of:
    molding a shell over a socket model and a mold dummy to form an intermediate port; and
    trimming the intermediate port along a trim line passing through a cavity defined by the mold dummy to create a circular opening in the shell, the mold dummy has a first diameter generally conforming to a diameter of a cylindrical extension of a housing of the access port;
    passing the cylindrical extension through the opening; and
    securing the access port to the shell.

2. The method of manufacturing a prosthetic socket of claim 1, wherein the housing of the access port includes a cylindrical flange and further comprising the step of compressing an O-ring seal between the cylindrical flange and the shell.

3. A method of manufacturing a prosthetic socket having an access port, the method of manufacturing comprising the steps of:
    providing a socket model;
    leveling an area of the socket model;

drilling a pilot hole in the level area of the socket model;
affixing a mold dummy piece to the socket model on the level area;
affixing a foam cover disk;
draping a heated molding material over the socket model and the mold dummy to mold a shell;
cooling the molding material to form a hard shell; and
removing surface material from the molding material to reveal an interface of the foam disk and the mold dummy.

4. The method of manufacturing a prosthetic socket of claim 3, further comprising the step of:
drilling a vacuum vent hole from a side opposite the mold dummy, through the socket model, up to the mold dummy.

5. The method of manufacturing a prosthetic socket of claim 3, wherein fixing the mold dummy is accomplished with a screw.

6. The method of manufacturing a prosthetic socket of claim 3, further comprising the step of:
removing the socket model and the mold dummy to reveal the molded shell.

7. The method of manufacturing a prosthetic socket of claim 6, further comprising:
finish sanding a land of the interface between the foam disk and the mold dummy to create a surface finish suitable for sealing with an O-ring seal.

8. The method of manufacturing a prosthetic socket of claim 3, further comprising the steps of:
removing the socket model;
installing an 0-ring seal within a cylindrical housing of the access port; and
inserting the cylindrical housing through the shell such that the 0-ring seal compresses against the interior surface of the shell.

9. The method of manufacturing a prosthetic socket of claim 8, further comprising the step of:
securing the access port to the shell.

10. A method of manufacturing a prosthetic socket having an access port, the method of manufacturing comprising the steps of:
providing a socket model, a mold dummy and a cover disk in a stack arrangement;
draping a formable material over the stack arrangement to form a shell;
removing a portion of the material at an interface of the cover disk and the mold dummy to define a circular opening in the shell;
inserting a housing having a cylindrical flange through the circular opening; and
securing the housing to the shell with a clamp nut on a side opposite to the housing insertion side.

11. The method of manufacturing a prosthetic socket of claim 10, further comprising the step of:
compressing a first 0-ring seal between the cylindrical flange and the shell.

12. The method of manufacturing a prosthetic socket of claim 11, further comprising the step of:
removing the socket model and the mold dummy upon completion of removing a portion of the material at an interface of the cover disk and the mold dummy.

13. The method of manufacturing a prosthetic socket of claim 12, further comprising the step of:
smooth sanding an outer surface of the shell adjacent the housing to provide a smooth surface for a second O-ring seal.

14. The method of manufacturing a prosthetic socket of claim 13, further comprising the step of: compressing the second O-ring seal between the shell and a clamp nut.

15. The method of manufacturing a prosthetic socket of claim 14, further comprising the step of:
simultaneously compressing the first and second 0-ring seals upon securing the housing with the clamp nut.

16. The method of manufacturing a prosthetic socket of claim 14, wherein an access plug of the access port defines a groove, and further comprising the step of:
inserting the access plug into the cylindrical housing from a side opposite an insertion side of the housing to compress a third 0-ring seal in the groove.

* * * * *